US011439306B2

(12) United States Patent
Themelis

(10) Patent No.: US 11,439,306 B2
(45) Date of Patent: Sep. 13, 2022

(54) APPARATUS AND METHOD FOR MEASURING BLOOD FLOW DIRECTION USING A FLUOROPHORE

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 551 days.

(21) Appl. No.: 16/224,962

(22) Filed: Dec. 19, 2018

(65) Prior Publication Data

US 2019/0200869 A1 Jul. 4, 2019

(30) Foreign Application Priority Data

Dec. 28, 2017 (EP) .................................... 17210909

(51) Int. Cl.
*A61B 5/00* (2006.01)
*A61B 5/026* (2006.01)
(Continued)

(52) U.S. Cl.
CPC ............ *A61B 5/0071* (2013.01); *A61B 5/026* (2013.01); *A61B 5/0261* (2013.01); *A61B 90/37* (2016.02);
(Continued)

(58) Field of Classification Search
CPC ........... A61B 5/0071; A61B 5/02; A61B 8/06; A61B 2090/376; A61B 5/026; G06T 2207/30104
See application file for complete search history.

(56) References Cited

U.S. PATENT DOCUMENTS

RE35,456 E * 2/1997 Yassa ........................ H04N 5/32
378/98.2
6,473,698 B1 * 10/2002 Albert .................. A61B 5/0261
702/19

(Continued)

FOREIGN PATENT DOCUMENTS

JP 2010154982 A 7/2010
JP 2017077413 A 4/2017
(Continued)

OTHER PUBLICATIONS

I. Kimura et al., "Temperature and Velocity Measurement of a 3-D Thermal Flow Field using Thermo-sensitive Liquid Crystals," Journal of Visualization, vol. 1, No. 2, pp. 145-152, Jun. 1998 (Year: 1998).*

(Continued)

*Primary Examiner* — Oommen Jacob
*Assistant Examiner* — Nyrobi Celestine
(74) *Attorney, Agent, or Firm* — Hodgson Russ LLP

(57) ABSTRACT

The invention relates to an apparatus (1) and method for automatically determining the blood flow direction (42) in a blood vessel (14) using the fluorescence light from a fluorophore (16). Blood flow direction (42) is determined by first identifying a blood vessel structure (38) in an input frame (6) from a camera assembly (2) using a pattern recognition module (26). Blood flow direction (42) is determined from the spatial gradient (dI/dx) of the fluorescence intensity (I) along the identified blood vessel structure (38) and the temporal gradient (dI/dt). An output frame (48) is displayed on a display (36) with time-varying marker data (52) overlaid on the identified blood vessels structure (38) and representative of the blood flow direction (42).

10 Claims, 3 Drawing Sheets

(51) Int. Cl.
*A61B 90/00* (2016.01)
*G06T 7/00* (2017.01)

(52) U.S. Cl.
CPC ...... *G06T 7/0012* (2013.01); *A61B 2090/376* (2016.02); *G06T 2207/30104* (2013.01)

(56) References Cited

U.S. PATENT DOCUMENTS

| | | | | |
|---|---|---|---|---|
| 6,480,615 | B1* | 11/2002 | Sun | G06T 7/248 382/103 |
| 10,722,173 | B2* | 7/2020 | Chen | A61B 5/0086 |
| 2004/0142485 | A1 | 7/2004 | Flower et al. | |
| 2010/0262017 | A1* | 10/2010 | Frangioni | A61B 5/0261 600/476 |
| 2013/0204127 | A1* | 8/2013 | Hoogi | A61B 8/481 600/431 |
| 2014/0236011 | A1* | 8/2014 | Fan | A61B 8/0891 600/440 |
| 2015/0208915 | A1 | 7/2015 | Schallek | |
| 2016/0015348 | A1 | 1/2016 | Ohishi | |
| 2016/0249874 | A1* | 9/2016 | Korporaal | A61B 6/486 382/131 |
| 2017/0112377 | A1 | 4/2017 | Shiba et al. | |
| 2017/0209031 | A1 | 7/2017 | Nakamura et al. | |
| 2017/0296140 | A1* | 10/2017 | Ebbini | A61B 8/485 |
| 2018/0085088 | A1* | 3/2018 | Du | G01S 15/8984 |
| 2018/0279874 | A1 | 10/2018 | Yoshida et al. | |
| 2020/0126219 | A1* | 4/2020 | Wang | G16H 30/20 |

FOREIGN PATENT DOCUMENTS

| | | | | |
|---|---|---|---|---|
| KR | 20090110600 | A | 10/2009 | |
| WO | WO-03030101 | A2* | 4/2003 | G06T 7/12 |
| WO | WO-2003030101 | A2* | 4/2003 | G06T 7/0012 |
| WO | WO-2015041312 | A1* | 3/2015 | A61B 5/7278 |
| WO | WO-2016061052 | A1* | 4/2016 | A61B 5/0261 |

OTHER PUBLICATIONS

G. J. Tearney et al., "Atherosclerotic Plaque Characterization by Spatial and Temporal Speckle Pattern Analysis," Optics Letters, vol. 27, No. 7, pp. 533-535, Apr. 2002 (Year: 2002).*

B. Weber et al., "Optical imaging of the spatiotemporal dynamics of cerebral blood flow and oxidative metabolism in the rat barrel cortex," European Journal of Neuroscience, pp. 1-7, Sep. 2004 (Year: 2004).*

A. Arzani et al., "Characterizations and Correlations of Wall Shear Stress in Aneurysmal Flow," Journal of Biomedical Engineering, vol. 138, pp. 014503-1-014503-10, Jan. 2016 (Year: 2016).*

T. Grus et al., "The Ratio of Diameters Between the Target Artery and the Bypass Modifies Hemodynamic Parameters Related to Intimal Hyperplasia in the Distal End-to-Side Anastomosis," Physiological Research, vol. 65, No. 6, pp. 901-908, Aug. 2016 (Year: 2016).*

Alessio et al., "Flow Evaluation of Red Blood Cells in Capillaroscopic Videos," Proceedings of the 26th IEEE International Symposium on Computer-Based Medical Systems, IEEE, Jun. 20, 2013, pp. 477-480.

Bitsch et al., "Micro particle-image velocimetry of bead suspensions and blood flows," Experiments in Fluids, 2005, vol. 39, No. 3, pp. 505-511.

Jensen et al., "Regional Variation in Capillary Hemodynamics in the Cat Retina," Investigatibe Ophthalmology & Visual Science, IOVS, 1998, vol. 39, No. 2, pp. 407-415.

Jeong et al., "Interaction between liposomes and RBC in microvessels in vivo," Microvascular Research, 2007, vol. 73, No. 1, pp. 39-47.

Kvon et al., "Development of dual micro-PIV system for simultaneous velocity measurements: optical arrangement techniques and application to blood flow measurements," Measurement Science and Technology, 2014, vol. 25, No. 7, 11 pages.

Majunatha et al., "Computerised visualisation from images of blood flow through frog mesenteric microvessels with multiple complexities," Medical & Biological Engineering & Computing, 2002, vol. 40, No. 6, p. 634-640.

Rouchdy et al., "A Geodesic Voting Method for the Segmentation of Tubular Tree and Centerlines," Proceedings of the 8th IEEE International Symposium on Biomedical Imaging: From Nano to Macro, 2011, 5 pages.

Suri et al., "A Note on Future Research in Vascular and Plaque Segmentation," Angiography and Plaque Imaging Advanced Segmentation Techniques, Biomedical Engineering Series, 2003, Chapter 12, pp. 502-530.

Zhong et al., "In vivo measurement of erythrocyte velocity and retinal blood flow using adaptive optics scanning laser ophthalmoscopy," Optics Express, 2008, vol. 16, No. 17, 16 pages.

* cited by examiner

APPARATUS AND METHOD FOR MEASURING BLOOD FLOW DIRECTION USING A FLUOROPHORE

CROSS REFERENCE TO RELATED APPLICATIONS

This application claims priority of European patent application number 17210909.2 filed Dec. 28, 2017, the entire disclosure of which is incorporated by reference herein.

FIELD OF THE INVENTION

The invention relates to an apparatus and a method for determining blood flow direction in a blood vessel using a fluorophore, in particular a bolus of a fluorophore.

BACKGROUND OF THE INVENTION

In neurosurgery, fluorescence angiography using indocyanine green (ICG) is commonly used to identify blood vessels in an operation area.

An experienced surgeon or assistant is able to distinguish different types of tissue in a video showing a time series of frames of image data which are acquired in the fluorescence spectrum of the fluorophore. For the identification of the blood vessels, the temporal and spatial development of fluorescence intensity is studied by the surgeon or assistant. This development allows to discern arteries, capillaries, veins and pathologic situations such as arterial-venous malformation by the surgeon or assistant.

The current cognitive analysis of videos of fluorescence images is, however, error-prone. Thus, there is a need to provide a apparatus and method for helping the surgeon or assistant to quickly understand visual information of an operation area during surgery.

SUMMARY OF THE INVENTION

The apparatus and method according to the invention aims to provide such assistance by automatically detecting blood vessels and the blood flow direction within these vessels, and by marking blood flow direction in output image data which are to be displayed to the user, such as a surgeon or assistant.

The apparatus according to the invention comprises
an input interface for retrieving at least one input frame of input image data in at least part of a fluorescence spectrum of the fluorophore,
a pattern recognition module for identifying at least one blood vessel structure within the input image data,
a computation module for determining the blood flow direction in the identified blood vessel structure from the spatial gradient along the identified blood vessel structure and the temporal gradient at at least one location in the identified blood vessel structure, and
an image generator module for computing at least one output frame of output image data, in which parts of the input image data corresponding to the identified blood vessel structure are overlaid with time-varying marker data, representative of the blood flow direction, and an output interface for outputting the output frame.

The above modules may be realized in hardware or software, or any combination of hardware and software.

The method according to the invention comprises the steps of
acquiring at least one input frame of input image data in at least part of the fluorescence spectrum of the fluorophore;
automatically recognizing at least one blood vessel structure within the at least one input frame;
determining the blood flow direction along the blood vessel structure from a spatial gradient of the fluorescence intensity along the identified blood vessel structure and the temporal gradient at at least one location (A) within the at least one identified blood vessel structure;
computing an output frame in which the blood vessel structure is overlaid with time-varying marker data; and
displaying the output frame.

Using input image data in at least part of the fluorescence spectrum of the fluorophore or, more preferably, input image data which are restricted to the fluorescence spectrum or part of the fluorescence spectrum of the fluorophore facilitates discerning the blood vessel structure from its surroundings which do not emit fluorescence. Using the fluorescence intensity distribution along the blood vessel structure allows identifying blood flow direction from a single frame, i.e. very quickly. Displaying the time-varying pattern allows visualizing blood flow direction to the user and, thus, facilitates orientation of the user in the operation area. The input image data preferably comprise pixel, wherein each pixel represents an area in a plane of the field of view. If the input image data are two-dimensional, there is only one such plane. If the input image data are three-dimensional at least two such planes exist in the input frame.

For the identification of the blood vessel structure and its geometry, known techniques such as described in "*Angiography and Plaque Imaging: Advanced Segmentation Techniques*" edited by Jasjit S. Suri, Swamy Laxminarayan, Apr. 29, 2003 by CRC Press, pages 501-518, can be used.

The apparatus and method according to the invention can be further improved by adding one or more of the features, which are described in the following. It is to be understood, that these features may be added independently of one another and that each of the features has a technical effect of its own. The following features may be used indiscriminately for both the method and the apparatus according to the invention.

For example, the reliability of the determination of the blood flow direction may be increased, if the computation module is adapted to compute a center line of the at least one identified blood vessel structure. Computing the center line of a structure is shown e.g. in Rouchdy, Youssef & Cohen, Laurent (2011), "*A geodesic voting method for the segmentation of tubular tree and centerlines*", Proceedings/IEEE International Symposium on Biomedical Imaging: from nano to macro. IEEE International Symposium on Biomedical Imaging. 979-983. 10.1109/ISBI.2011.5872566. The center line may be used to simplify subsequent computations, as the identified blood vessel structure may be reduced to the center line, i.e. be reduced from a two-dimensional array of input image data or pixels to a one-dimensional array. The at least one location may be located on the center line.

An input frame may be a frame as acquired by the camera assembly or be computed from a plurality of frames, e.g. to reduce sensor or amplifier noise in low-light conditions or areas.

The input frame may be retrieved by the input interface from a camera or from a storage assembly, e.g. a memory device, where the input frames are buffered or stored after pre-processing.

The computation of at least one of the fluorescence intensity distribution, the spatial gradient and the temporal gradient along the center line reflects more accurately the spatial development of fluorescence intensity along the blood vessel structure than e.g. the distribution close to the walls of the identified blood vessel structure. In this context, the center line is of the identified blood vessel structure is represented by an array of pixels which in turn represent areas of the field of vision which overlap with the center line of the actual blood vessel.

The blood vessel structure may be identified using solely fluorescent light. In addition or alternatively, the blood vessel structure may be identified by comparing the spectrum at one pixel in the input image data to the reflectance spectrum of at least one of arterial and venous blood.

In one embodiment of the apparatus and/or the method according to the invention camera assembly may be provided, the camera assembly having a field of view and being adapted to acquire at least one input frame of input image data in at least part of a fluorescence spectrum of the fluorophore, the input image data representing the field of view, particularly at a given time. The camera assembly may be connected to the input interface. The camera assembly may be at least one of a RGB camera assembly, a multispectral camera assembly and a hyperspectral camera assembly. Preferably, at least one array of sensors is dedicated for acquiring image data in a spectrum which is restricted to the fluorescence spectrum of the fluorophore.

Additionally or alternatively, the apparatus and/or method may provide a user interface, which allow the user to mark specific parts of the input image data as a blood vessel structure. Such a graphical user interface may be part of the pattern recognition module. For example, the user may define any preferably coherent array of pixels as a blood vessel structure. This structure is then treated just like an automatically recognized blood vessel structure. Alternatively or additionally, the user may enter a line of pixels which then is treated as the center line. If such a manual input is used, the automatic identification of the blood vessel structure and of the center line may not be needed.

In another embodiment, at least one of the fluorescence intensity, the temporal gradient and the spatial gradient at a location on the center line of the blood vessel structure—i.e. at a pixel representing this location—may be computed from an average in a preferably coherent array of pixels or input image data adjacent or surrounding the pixel or input image data. The pixels or, equivalently, the input image data of the array may in particular be located along a line which extends from the pixel perpendicular to the center line across the identified blood vessel structure. The line may have a width of one or more pixels in the direction along the identified blood vessel structure or along the center line. The line preferably extends across the entire width of the identified blood vessel structure in a direction perpendicular to the center line. Averaging the fluorescence intensities of an array further improves the accuracy of computing the fluorescence intensity distribution, as both noise and an uneven fluorescence intensity distribution across the blood vessel structure may be eliminated.

To reduce noise and artifacts, a curve fit may be computed for at least one of the fluorescence intensity, the spatial gradient and the temporal gradient. Such a curve fit may be a polynomial fit, a low-pass filtering, or a principal component analysis. The fitting may further reduce noise in the fluorescence intensity data. The fluorescence intensity, the spatial gradient and/or the temporal gradient may be filtered using temporal and/or spatial filters such as low-pass or band-pass filter to remove outliers.

The at least one location may be a single pixel or an array of pixels in the input image data. Preferably, the spatial and temporal gradients are computed at a plurality of locations which are spaced apart from each other along the identified blood vessel structure. The at least one location is preferably located on the center line of the identified blood vessel structure. For example, the spatial gradient and the temporal gradient may be computed at every pixel in the input frame and/or input image data, along the blood vessel structure, in particular on every pixel on the center line.

The temporal gradient may be computed using the fluorescence intensity at at least two matching locations within the identified blood vessel structure of at least two subsequent input frames of the time series of input frames. Again, the location corresponds to one pixel or an array of pixels in the input image data. The location is preferably situated on the center line. Preferably, the at least one location where the temporal gradient is computed corresponds to the at least one location where also a spatial gradient is computed in at least one of the input frames.

In the apparatus, the computation of at least one of the spatial and temporal gradient may be carried out by the computation module.

The step of identifying a blood vessel structure and/or of computing the temporal gradient may include the step of identifying a matching location within the identified blood vessel structure in at least two subsequent frames. It may further include matching a location on the center line of the identified blood vessel structure in one input frame of a time series to a location on the center line of the identified blood vessel structure in a subsequent or preceding input frame of the time series. These steps may be carried out by the pattern recognition module of the apparatus.

In the step of comparing the spatial gradient to the temporal gradient, the locations of the spatial gradient and the respective temporal gradient which are compared are identical. The comparison may be carried out respectively at a plurality of locations. In the apparatus, the computation module may be configured for this comparison.

Under the following assumption, the blood flow direction can be computed with very little computation effort and high accuracy by performing a quadrant analysis of the temporal and spatial gradient at at least one location. The quadrant analysis may include comparing the signs of the temporal gradient and the spatial gradient at the at least one location.

If the field of view of the camera assembly is sufficiently small, the bolus of the fluorophore can be regarded as a wave of fluorescence intensity propagating along the identified blood vessel structure with the respective blood flow velocity in an unaltered shape. Thus, the fluorescence intensity I which in general is a function of both time, t, and space, (X, Y, Z), i.e. I(X, Y, Z), can be reduced to a one dimensional intensity wave function, $$I(X,Y,Z,t)=I(x+vt), \tag{1}$$

where x is a coordinate measured along the blood vessel and v is the propagation velocity of the fluorescence wave, i.e. the blood flow velocity. In eq. (1), I(x−vt) indicates a fluorescence wave propagating in the positive x direction and I(x+vt) indicates a fluorescence wave propagating in the negative x direction along the blood vessel structure, in particular along its center line.

From equation (1) the relationship of the spatial gradient, dI/dx, of the fluorescence intensity to the temporal gradient, &Mt, of the fluorescence intensity can be derived as $$dI/dx \pm \pm v^* dI/dt. \qquad (2)$$

In equation (2), the + sign applies if the bolus travels in the negative x-direction and the sign applies if the bolus travels in the positive x-direction along the blood vessel. This relationship holds independent of how the direction of x has been defined. From equation (2), it follows that if the spatial gradient has a different sign than the temporal gradient at a location, the fluorescence intensity waves travels in the negative x direction, and thus the blood flow direction is directed along the positive x-direction; if the spatial gradient and the temporal gradient have the same sign, blood flow direction is in the negative x direction.

The step of determining blood flow direction may include comparing the signs of the temporal gradient and the spatial gradient at at least one location of the identified blood vessel structure or a center line. The comparison may comprise an arithmetic operation, such as a subtraction, and/or a logic operation, such as sign bit masking or larger than/small than comparison.

If the comparison is carried out at a plurality of locations in an input frame the determination of the blood flow direction becomes more reliable. For example, the blood flow direction may be determined to be in the positive direction if, at the majority of locations, the spatial gradient and the temporal gradient have opposite signs. Known statistical methods may be used to improve the reliability of this estimation, such as using only gradients which fall within a predetermined range of values or where at the same time the fluorescence intensity is within a predetermined range. In the apparatus, the computation module may be configured to carry out any of the preceding steps.

In view of the above, the step of identifying the blood vessel structure may also include the step of defining a positive direction along the identified blood vessel structure, in particular along its center line. In the apparatus, the pattern recognition module may be configured for this definition.

The time-varying marker data may comprise at least one visible sub-structure which changes location from one output frame to a subsequent output frame along the blood vessel structure in the blood flow direction. The sub-structure may be an in particular coherent set of image data which is distinguished from a neighboring sub-structure of the marker data by at least one of brightness and color. For example, the sub-structure may be a stripe which extends perpendicularly to the center line and is neighbored by stripes which have at least one of different brightness and different color. The change in location of the sub-structure along the blood vessel structure or the center line from one output frame to the next output frame is preferably smaller than the extent of the sub-structure along the blood vessel structure or its center line.

The above features may be implemented in software, in hardware or in any combination of software and hardware components. The invention may further relate to a non-transitory computer-readable medium storing a program causing a computer to execute the method in any of the above-described embodiments. In the following, an exemplary embodiment of the invention is described with reference to the drawings. In the drawings, the same reference numeral is used for elements that correspond to each other with respect to at least one of design and function. Moreover, it is clear from the above description, that technical features may be added to the exemplary embodiment if, for a particular application, the technical effect associated with that feature is useful. Vice versa, a feature shown in the exemplary embodiment may be omitted if the technical effect associated with that feature is not needed for a particular application.

BRIEF DESCRIPTION OF THE DRAWING VIEWS

In the figures.

DETAILED DESCRIPTION OF THE INVENTION

Figure 1:
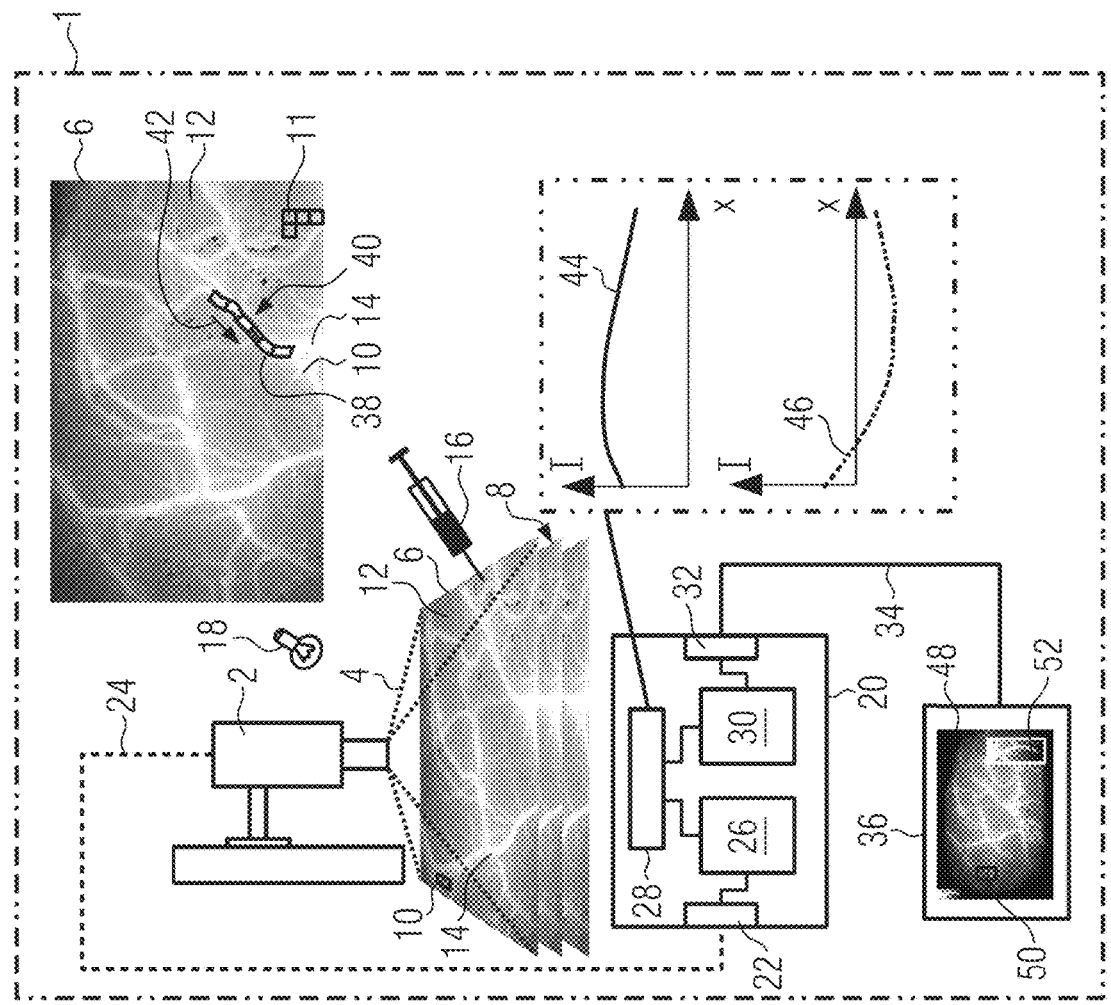
FIG. 1 shows a schematic view of an apparatus according to the invention.

First, the structure of an apparatus 1 for measuring blood flow direction. Apparatus 1 may in particular be a microscope or endoscope.

The apparatus 1 comprises a camera assembly 2, which may comprise at least one of an RGB, multi-spectral camera or hyper-spectral camera. The camera assembly 2 has a field of view 4 of which it acquires at least one input frame 6 or a time-series 8 of input frames 6. An input frame 6 consists of image data 10, which in turn may include pixels 11. Each input frame 6 represents a rendition of the field of view 4 at a moment of time. Each pixel 10 represents a portion of the field of view 4.

In FIG. 1, live tissue 12 has been arranged in the field of view 4, for example to perform brain or blood vessel surgery, which may be assisted by apparatus 1.

To identify blood vessels 14 in the live tissue 12 or, respectively, its digital representation, namely, the input frame 6 or the input image data 10, a fluorophore 16 has been injected into live tissue 12. This results in a bolus of the fluorophore which is transported with the blood flow. An example for such a fluorophore 16 is indocyanine green, ICG.

An illumination assembly 18 may be provided to illuminate the field of view 4 with light comprising or being restricted to wave lengths which trigger fluorescence of the fluorophore 16.

The camera assembly 2 is configured to acquire the at least one input frame 6 in at least part of the fluorescence spectrum of the fluorophore 16. Preferably, the wave lengths which are represented in the input frame 6 are restricted to the fluorescence spectrum of the fluorophore 16. The camera assembly 2 may comprise an additional camera (not shown), to simultaneously acquire input frames in the visible light range. If a multi- or spectral camera assembly is used, visible light and fluorescence light frames may be recorded simultaneously.

By recording the frames in the fluorescence spectrum of the fluorophore 16, the blood vessels 14 can be clearly discerned from surrounding tissue, as the fluorescence intensity will be highest in regions which gather most of the fluorophore 16 i.e. in blood vessels.

The input frame 6, and thus the input image data 10 may be stereoscopic, three-dimensional or multidimensional. In a multidimensional frame, a pixel 11 may be located in one place of the input frame. Using a microscope, three-dimensional input image data 10 may be acquired using for example, z-stacking, scape or skim microscopes. Multidimensional input image data 10 may be generated by a multispectral or hyperspectral camera.

The apparatus 1 may further comprise an image processing assembly 20, such as at least one integrated circuit.

The image processing assembly 20 may comprise an input interface 22 for inputting at least one input frame 6 and/or input image data 10, respectively. The input interface 22 may be in a data-transferring connection 24, such as a wired or wireless data connection, to the camera assembly 2. The image processing assembly 20 may comprise a pattern recognition module 26, a computation module 28 and an image generator module 30, which are thus, also directly part of apparatus 1. Further, an output interface 32 may be provided. A wired and/or wireless data connection 34 may be provided to connect at least one display 36 to output interface 32.

The input frame 6 or time series 8 of input frames 6 may be input to the pattern recognition module 26. The pattern recognition module 26 is configured to identify at least one blood vessel structure 38 in the input frame 6 or input image data 10, respectively. Such an identification may be performed with known algorithms such as described in "*Angiography and Plaque Imaging: Advanced Segmentation Techniques*" edited by Jasjit S. Suri, Swamy Laxminarayan, Apr. 29, 2003 by CRC Press, pages 501-518.

The computation module 28 is connected to the pattern recognition module 26 and may receive a digital representation 40 of the blood vessel structure 38, which herein is also termed as identified blood vessel structure 38. The identified blood vessel structure 38 may, for example, comprise or consist of those input image data 10 and/or pixels 11 which represent the blood vessel 14 in the field of view 4.

The computation module is configured to determine the blood flow direction 42 from the fluorescence intensity distribution 44 along the blood vessel structure 38. In particular, the computation module 28 may be configured to compute the spatial gradient 46, dI/dx, of the fluorescence intensity I along the identified blood vessel structure 38.

The image generator module 30 is configured to compute at least one output frame 48 of output image data 49, such as output pixels 50. The image generator module 30 may, in particular, be configured to generate a time-series of output frames 48 from one or more input frames 6. In the output frames 48, parts of the input image data 10 that correspond to the identified blood vessel structure 38 may be overlaid with time-varying marker data 52. The time-varying marker data 52 are thus used to indicate both the blood vessel structure 38 and blood flow direction 42.

The terms pattern recognition module, computation module and image generator module are used primarily to differentiate them functionally. These modules can be part of the same electrical component or of the same software element, e.g. subroutine.

The at least one output frame 48 is then displayed on at least one display 36, which may be a monitor which can be observed by several persons and/or a display in a microscope, which is viewed through an ocular.

Figure 2:
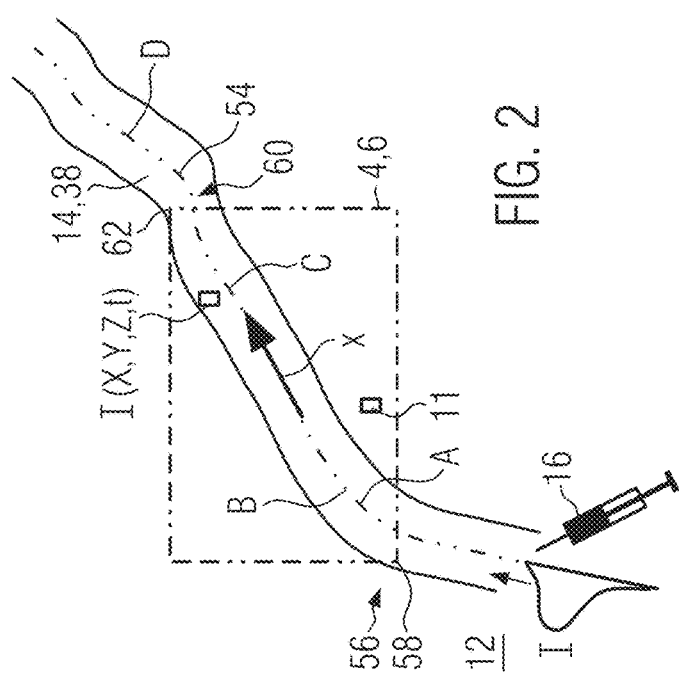
FIG. 2 shows a schematic rendition of another identified blood vessel structure.

FIG. 2 shows a blood vessel 14 or its digital representation, the identified blood vessel structure 38. A positive x-direction has been determined along the blood vessel structure 38, e.g. by the pattern recognition module. This can be done e.g. by requiring that the positive x-direction is directed from an end 56 of the blood vessel structure which is closer to one corner 58 of the input frame 6 to the opposite end 60 of the blood vessel, which is closer to the diagonally opposed corner 62 of the input frame. The positive x-direction can also be determined by first computing a center line 54 of the blood vessel structure 38 and then determining the positive x-direction using the distance of the ends of the center line 54 to corners 58, 62. The center line may be computed by connecting the pixels 11, which are located in the middle of the smallest widths of the blood vessel structure 38, or as described in Rouchdy, Youssef & Cohen, Laurent. (2011), "*A geodesic voting method for the segmentation of tubular tree and centerlines*", Proceedings/IEEE International Symposium on Biomedical Imaging: from nano to macro. IEEE International Symposium on Biomedical Imaging. 979-983. 10.1109/ISBI.2011.5872566.

As further shown in FIG. 2, a bolus of a fluorophore 16 is somewhere into the live tissue 12. The bolus is then transported with the blood flow and eventually reaches the blood vessel 14.

The blood flow direction 42 can then be computed from the fluorescence intensity distribution along the blood vessel structure as e.g. represented by the positive x direction.

One embodiment of the determination of the blood flow direction 42 is as follows looking at the two locations A and B which are spaced apart from one another along the blood vessel structure 38. In particular, locations A and B may be located at the center line 54. B may be further in the positive x-direction than A.

If the bolus travels along the blood vessel 14 in the positive x direction, the fluorescence intensity will first increase at location A and then at location B. As long as the fluorescence intensity maximum has not passed location A, the fluorescence intensity at location A will be larger than at location B.

Thus, the temporal gradient location A will be positive as long as the fluorescence intensity maximum has not passed location A. In its simplest form, the temporal gradient at location A is the difference of the fluorescence intensity at location A in a later input frame 6 of the time series 8 and of the fluorescence intensity at the same location A at an earlier input frame 6 of the time series 8. The location A may be tracked over subsequent input frames by e.g. defining a location A by its relative position along the total length of the center line 54. The same holds for the temporal gradient at any other location.

At the same time, the spatial gradient of the fluorescent intensity at location A will be negative, as long as the fluorescence intensity maximum has not passed location A, because the fluorescence intensity at location A will be larger than at any downstream location, such as location B. The spatial gradient at location A may, in its simplest form be the difference between the fluorescence intensity at location A and at least one downstream and/or upstream location such as A. The same holds for the spatial gradient at any other location.

After the fluorescence intensity maximum has passed location A, the fluorescence intensity will decrease over time at location A. Thus, the temporal gradient at location A will be negative. At the same time, the fluorescence intensity at any downstream location, such as location B, will be larger than at location A. This results in a positive spatial gradient at location A.

Thus, if, at a location A in the identified blood vessel structure 38, the temporal gradient and the spatial gradient are of opposite sign, the blood flow direction 42 is in the positive direction at this location. Therefore, determining the blood flow direction 42 preferably comprises comparing the spatial gradient at a location to the temporal gradient at this location.

If the bolus travels along the blood vessel 14 in the negative x direction, the fluorescence intensity will first increase over time at location A and when the maximum fluorescence intensity has passed location A, then the fluorescence intensity will decrease over time at location A. Thus, the temporal gradient at location A will first be positive and then turn negative after passage of the fluorescence intensity maximum. The spatial gradient at location A will also be first positive, as fluorescence intensity will increase in the downstream direction and, after passage of the fluorescence intensity maximum, turn negative.

Thus, if, at a location in the identified blood vessel structure 38, the spatial gradient and the temporal gradient are of the same sign, the blood flow direction 42 is in the negative x direction. This corresponds to result of equation (2) above.

Thus, determining blood flow direction 42 may be simplified to a simple quadrant analysis of the signs of the spatial and temporal gradients at at least one location in the identified blood vessel structure 38. In this context, it is to be noted that, numerically, at least two points in the spatial direction and the temporal directions, respectively, need to be used to compute the temporal and spatial gradients at one location. The fluorescence intensity wave is travelling in the positive x-direction if the spatial and the temporal gradients at the location in the blood vessel structure 38 have different signs. The fluorescence intensity wave is travelling in the negative x-direction if, at a given location in the blood vessel structure 38, both the temporal and spatial gradient have the same sign.

The spatial gradient and the temporal gradient may be computed for any number of locations within the identified blood vessel structure 38. The blood flow direction 42 within the blood vessel structure may be defined to correspond to the average blood flow direction 42 as computed over all locations where the spatial and temporal gradient has been determined. The average may be weighted, e.g. by the fluorescence intensity at a particular location or by its distance from the center line. This approach eliminates any uncertainty which may result from using only a few locations if the maximum of fluorescence intensity just passes the few locations. Preferably at least two locations are used which are located at or close to the ends of the identified blood vessel structure, and possibly a third location in the middle of the x direction. The most reliable results can be obtained if the blood flow direction 42 is computed at every location in the identified blood vessels structure 38 or along the center line 54.

The computation of the fluorescence intensity distribution along the center line 54 can be made more accurate, if the fluorescence intensity at a location such as A is computed as the average of the fluorescence intensities of a preferably coherent array 70 of neighboring pixels 11 in the respective input frame 6.

Figure 3:
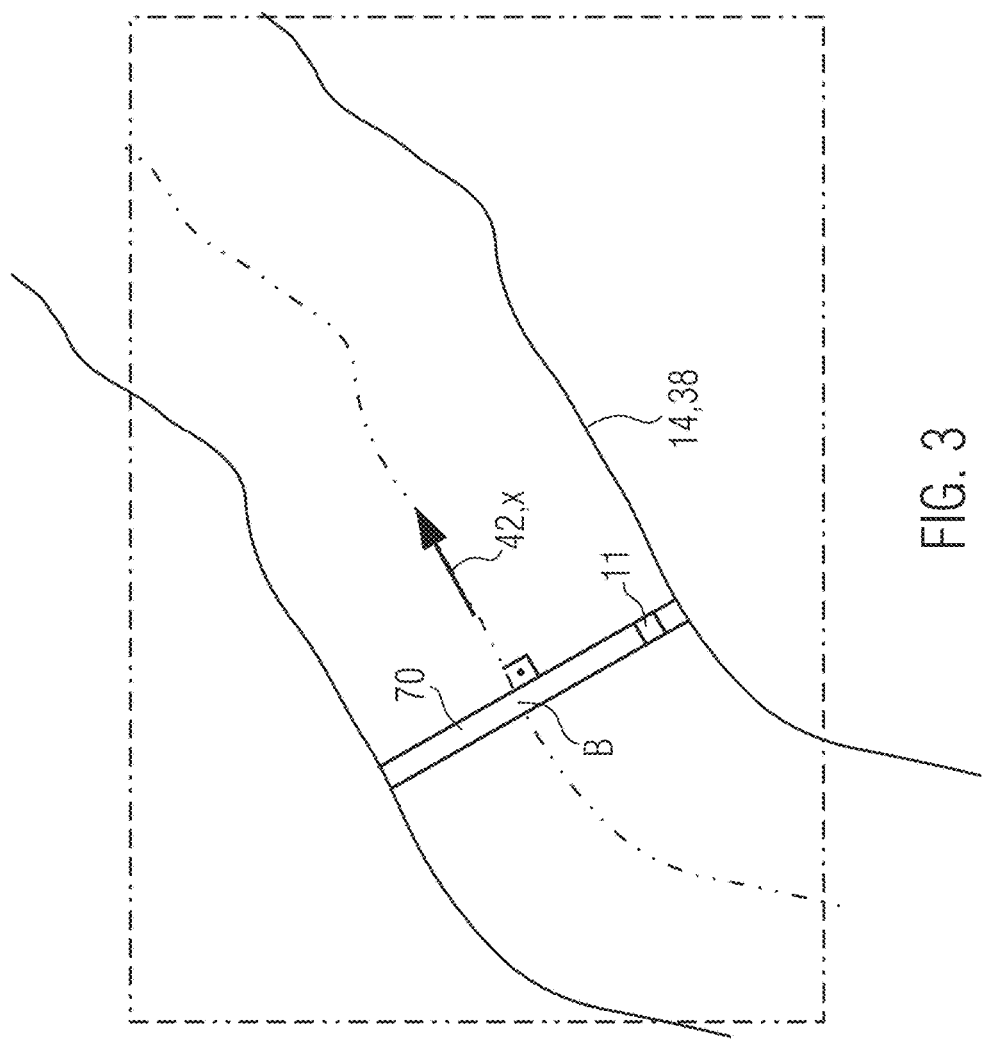
FIG. 3 shows a schematic rendition of another identified blood vessel structure.

It is preferred that the locations for which the spatial and temporal gradients are computed are located on the center line 54. In this case the array 70 of pixels 11 may extend perpendicular to the center line 54, and be e.g. a strip of pixels which has a width along the center line of at least one pixel. This is shown in FIG. 3. The array 70 may extend across part of or the entire width of the indentified blood vessel structure perpendicular to the center line 54 and may represent a cross section of the blood vessel 14 which is represented by the identified blood vessel structure.

The average can be a geometric, median, weighted or arithmetic mean value of the fluorescence intensities array 70.

To reduce noise, a curve fit may be computed to the fluorescence intensity distribution along the center line 42 of the identified blood vessel structure 38 in a frame. The curve fit may be e.g. a polynomial fit, or a principal component analysis may be performed. Alternatively, an analytic model of the fluorescence intensity shape can be adapted to the computed fluorescence intensity distribution. The fluorescence intensity distribution may be spatially filtered using a low-pass or band-pass filter to remove outliers.

Alternatively or additionally, such a curve fit and filtering may also be computed for at least one of the spatial gradient distribution and the temporal gradient distribution in the identified blood vessel structure 38 in the input frame 6.

The computation of the curve fit may be done in the computation module 28.

Once the blood flow direction 42 has been computed for the identified blood vessel structure 38, information representing the blood flow direction 42 may overlaid onto the input image data 10 in the output image data 49.

Figure 4:
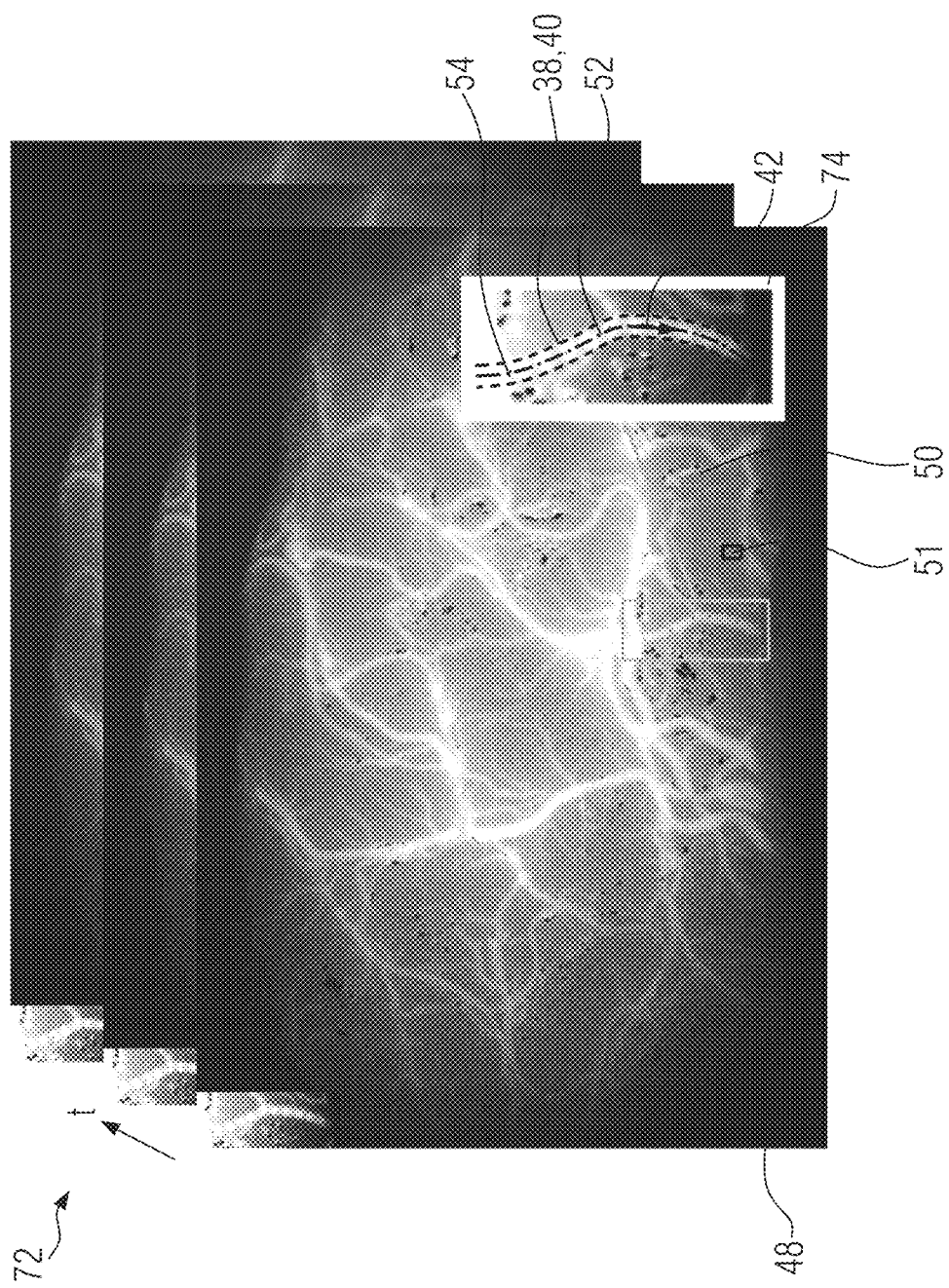
FIG. 4 shows a schematic rendition of output frames.

This becomes clear from FIG. 4, where an output frame 48 and, respectively, a time series 72 of output frames 48 is shown. An inlay 74 shows an enlarged part of the output image data 49, in which the blood vessel structure 38 has been overlaid with the time-varying marker data 52. The inlay may not be part of the output image data 49. The time-varying marker data may include false colors.

Between one output frame 48 and at least one of the subsequent output frames in the time series 72, the location of the time-varying marker data 52 within the blood vessel structure 38 is shifted in the blood flow direction 42. Preferably, the amount, in which the marker data 52 are shifted between subsequent output frames of the time series 72 is smaller than the extent of the marker data in the blood flow direction, so that the marker data gradually progresses along the blood flow direction 42.

The marker data 52 may differ from its adjacent regions in the blood vessel structure 38 by at least one of color and brightness. Preferably, the marker structure 52 extends across the whole width of the blood vessels structure 38 in the direction perpendicular to the center line 54 of the blood vessel structure 38.

REFERENCE NUMERALS

1 Apparatus
2 Camera assembly
4 Field of view
6 Input frame
8 Time series of input frames
10 Input image data
11 pixel
12 Live tissue
14 Blood vessel
16 Fluorophore
18 Illumination assembly
20 Image processing assembly
22 Input Interface
24 Data connection between camera assembly and image processing assembly
26 Pattern recognition module
28 Computation module
30 Image generator module
32 Output interface
34 Data connection
36 Display
38 (identified) Blood vessel structure
40 Digital representation of blood vessel structure 42 Blood flow direction
44 Fluorescence intensity distribution
46 Gradient of fluorescence intensity distribution
48 Output frame
49 Output image data
50 Output pixel
52 Time-varying marker data
54 Center line of blood vessel structure
56 End of blood vessel structure
58 Corner of input image
60 End of blood vessel structure
62 Corner of input image
70 Array of pixels
72 time series of output frames
74 inlay
I Fluorescence intensity
X, Y, Z Cartesian coordinates in the field of view
x coordinate along center line of blood vessel structure
t time
v blood flow velocity in blood vessel structure

What is claimed is:

1. An apparatus for measuring blood flow direction using a fluorophore, the apparatus comprising:
an input interface for retrieving at least one input frame of input image data in at least part of a fluorescence spectrum of the fluorophore;
one or more processors configured to:
identify at least one blood vessel structure within the input image data;
determine a blood flow direction in the identified blood vessel structure by comparing signs of a spatial gradient of fluorescence intensity along the identified blood vessel structure and a temporal gradient of fluorescence intensity at at least one location in the identified blood vessel structure; and
compute at least one output frame of output image data, in which parts of the input image data corresponding to the identified blood vessel structure are overlaid with time-varying marker data representative of the blood flow direction; and
an output interface for outputting the output frame;
wherein the one or more processors are further configured to define a positive direction along the identified blood vessel structure and determine the blood flow direction is along the positive direction if the temporal gradient and the spatial gradient have opposite signs;
wherein the temporal gradient is a difference between fluorescence intensity in a later input frame and an earlier input frame at the at least one location, and the spatial gradient is a difference between fluorescence intensity at the at least one location and a downstream location.

2. The apparatus according to claim 1, wherein the one or more processors are further configured to compute a center line of the at least one identified blood vessel structure and wherein the at least one location is located on the center line.

3. The apparatus according to claim 1, wherein the one or more processors are further configured to compute the spatial gradient from an average fluorescence intensity of an array of pixels in the input frame.

4. The apparatus according to claim 3, wherein the one or more processors are further configured to compute a center line of the at least one identified blood vessel structure and wherein the array of pixels extends perpendicularly to the center line across at least part of the identified blood vessel structure.

5. The apparatus according to claim 1, wherein the one or more processors are further configured to compute a curve fit to at least one of: i) the fluorescence intensity distribution along the identified blood vessel structure or a center line of the identified blood vessel structure, ii) the spatial gradient, and iii) the temporal gradient.

6. A method for determining blood flow direction in a blood vessel using a fluorophore, the method comprising the steps of:
acquiring at least one input frame of input image data in at least part of the fluorescence spectrum of the fluorophore;
automatically recognizing at least one blood vessel structure within the at least one input frame;
determining a blood flow direction along the blood vessel structure by comparing signs of a spatial gradient of a fluorescence intensity along the identified blood vessel structure and a temporal gradient of fluorescence intensity at at least one location within the at least one identified blood vessel structure, wherein a positive direction along the identified blood vessel structure is defined and the blood flow direction is determined to be along the positive direction if the temporal gradient and the spatial gradient have opposite signs;
computing an output frame, in which the blood vessel structure is overlaid with time-varying marker data; and
displaying the output frame;
wherein the temporal gradient is a difference between fluorescence intensity in a later input frame and an earlier input frame at the at least one location, and the spatial gradient is a difference between fluorescence intensity at the at least one location and a downstream location.

7. The method according to claim 6, wherein the step of automatically recognizing at least one blood vessel structure comprises the step of determining a center line of the blood vessel structure.

8. The method according to claim 6, wherein the step of determining the blood flow direction comprises the step of computing the fluorescence intensity at the at least one location by averaging the fluorescence intensity of an array of pixels.

9. The method according to claim 7, wherein the step of determining the blood flow direction comprises the step of computing a curve fit to at least one of the fluorescence intensity, the spatial gradient, and the temporal gradient at least along the identified blood vessel structure or the center line.

10. A non-transitory computer-readable medium storing a program causing a computer to execute the method according to claim 6.

* * * * *